United States Patent
Lin

(10) Patent No.: US 7,147,728 B2
(45) Date of Patent: Dec. 12, 2006

(54) MAGNESIUM ALLOY PRODUCING NEGATIVE POTENTIAL

(75) Inventor: Ming-Zhu Lin, Kaohsjung (TW)

(73) Assignee: Lightwave Nano Biotech Co., Ltd., Kaohsjung (TW)

( * ) Notice: Subject to any disclaimer, the term of this patent is extended or adjusted under 35 U.S.C. 154(b) by 0 days.

(21) Appl. No.: 10/974,157

(22) Filed: Oct. 27, 2004

(65) Prior Publication Data
US 2006/0086433 A1 Apr. 27, 2006

(51) Int. Cl.
*C22C 23/00* (2006.01)
*B01D 37/02* (2006.01)

(52) U.S. Cl. ............... 148/420; 420/409; 210/192; 210/193; 210/263

(58) Field of Classification Search ........ 420/409; 148/420; 210/192, 193, 263
See application file for complete search history.

(56) References Cited

U.S. PATENT DOCUMENTS 3,653,880 A * 4/1972 Gitlesen ............... 420/408
3,947,268 A * 3/1976 Tikhonova et al. ......... 420/409

FOREIGN PATENT DOCUMENTS

| JP | 09157782 | * | 6/1997 |
| JP | 2000204453 | * | 7/2000 |

OTHER PUBLICATIONS

Hoppel, H.W.; Eisenmeier, G.; Holzwarth, B.; Mughrabi, H., Cyclic deformation behavior of the cast magnesium alloy AZ91, Magnesium Alloys and their applications, Munich, Germany, Sep. 27-28, 2000, 348-353. ISBN:3-527-30282-4.*
Mabuchi, M.; Yamada, Y.; Shimojima, K.; Wen, C.E.; Chino, Y.; Nakamura, M.; Asahina, T.; Iwasaki, H.; Aizawa, T. Higashi,K. The grain size dependence of strength in the extruded AZ91 Mg alloy, Sep. 27-28, 2000, 348-353. ISBN:3-527-30282.*

* cited by examiner

*Primary Examiner*—Sikyin Ip

(57) ABSTRACT

A type of magnesium alloy that is capable of producing negative potential, characterized in that it contains 8 wt %~9.1 wt % of aluminum (Al), 0.1 wt %~1.0 wt % of zinc (Zn), 0.1 wt %~1.0 wt % of manganese (Mn), 0.05 wt % or less of silicone (Si), 0.002 or less of iron (Fe), 0.0012 wt % or less of copper (Cu), 0.0009 wt % or less of nickel (Ni) and 0.0008 wt % or less of beryllium (Be), the negative potential magnesium alloy binds with calcium ions and magnesium ions to show a pH value of water quality on the alkaline side.

8 Claims, 1 Drawing Sheet

MAGNESIUM ALLOY PRODUCING NEGATIVE POTENTIAL

BACKGROUND THE INVENTION

1. Background of the Invention

The present invention relates to a magnesium alloy producing negative potential, particularly to magnesium alloy that is used to produce negative potential in negative potential magnesium ion containers and reverse osmosis RO drinking water containers.

2. Description of the Prior Art

The filter device normally installed inside a drinking machine often uses a plastic container containing filtering materials to improve the quality or PH value of water, including anti-bacteria ceramics, calcium ion, bamboo coal, energy stones, infrared ray substances and alkaline ceramics, which are used to change the composition of ingredients and the PH value of water. But they lack the substances that produce negative potential in water, so they are unable to bring about other matters to change the water quality.

SUMMARY OF THE INVENTION

The present invention relates to a magnesium alloy producing negative potential, to improve water quality and obtain alkaline water with negative potential, containing the main ingredients such as aluminum, zinc, manganese, silicone, iron, copper, nickel, beryllium and magnesium. They are compressed to form a product that is combined with magnesium ion and calcium ion to form a medium layer. The infrared substances, bamboo coal, anti-bacteria ceramics, energy ceramics and tourmaline form an upper layer. Alkaline ceramic particles form a bottom layer. The upper layer, medium layer and bottom layer bind to form a negative potential magnesium ion layer, thereby obtaining a water quality containing negative potential and having a PH value at 8~11. Moreover, the present invention of magnesium alloy producing negative potential can be coated on other matters to improve the water quality.

BRIEF DESCRIPTION OF THE DRAWINGS

The other objects and features of the present invention can be more fully understood by referring to the following description of the preferred embodiments and accompanying drawings, in which.

DETAILED DESCRIPTION OF THE PREFERRED EMBODIMENT

Figure 1:
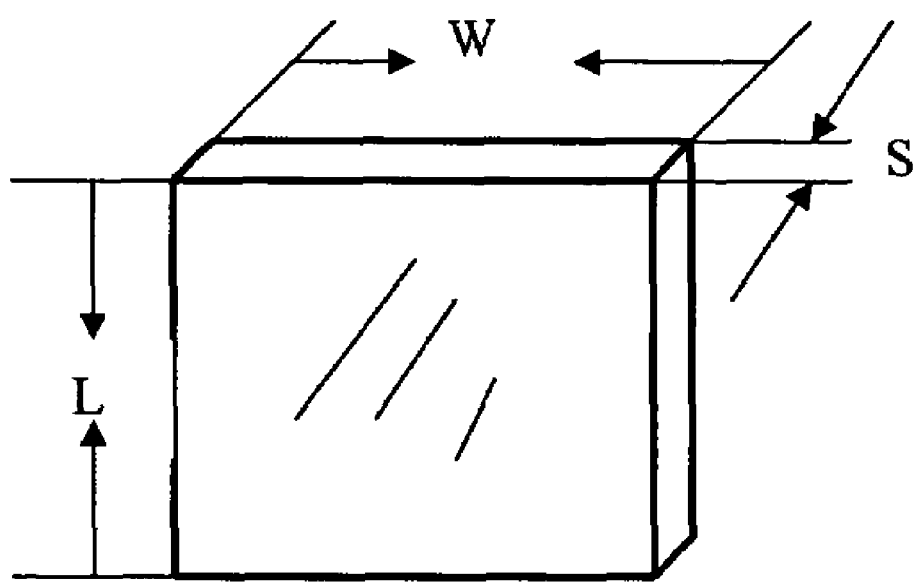
FIG. 1 is a schematic view of the present invention.

The present invention relates to a magnesium alloy producing negative potential. To obtain the magnesium alloy that is capable of producing negative potential, the present invention is characterized in that; it contains 5 wt %~9.1 wt % of aluminum (Al), 0.1 wt %~1.0 wt % of zinc (Zn), 0.1 wt %~1.0 wt % of manganese (Mn), 0.05 wt % or less of silicone (Si), 0.002 wt % or less of iron (Fe), 0.0012 wt % or less of copper (Cu), 0.0009 wt % or less of nickel (Ni) and 0.0008 wt % or less of Beryllium (Be).

Using the properties of magnesium alloy when compressed to form, it is capable of satisfying rigorous requirements in terms of tensile strength, flexibility maximum stress, extensibility, and resistance to corrosion.

Suppose we set aluminum at a reading ranging between 5 wt % and 9.0 wt %; when aluminum is less than 5 wt %, it will not have sufficient mechanical properties; if it is set at more than 9 wt %, it will not have a negative potential status better than the prior art. Suppose we set aluminum at a reading ranging between 0.6 wt % and 1 wt %; if zinc is less than 0.1 wt %, it has poor resistance to corrosion; if it is more than 1 wt %, it will not achieve a better negative potential status.

Suppose manganese is set at a reading ranging between 0.1 wt % and 1 wt %, it has excellent resistance to corrosion; if manganese is less than 0.1 wt %, its resistance to corrosion will deteriorate significantly; if it is more than 1 wt %, it is not likely to have better negative potential status.

For the purpose of producing negative potential, the present invention of magnesium alloy preferably contains the following ingredients: 6 wt %~9 wt % of aluminum, 0.65 wt %~1 wt % of zinc, 0.22 wt % of manganese, 0.0010 wt %~0.0012 wt % of copper, 0.01 wt %~0.03 wt % of silicone, 0.0020 wt % of iron, 0.0008 wt % or less of nickel, 0.0008 wt % or less of beryllium, and the remaining percentage of magnesium.

EXAMPLES

As shown in the composition of examples 1~3 in Table 1, the specified percentages of aluminum, zinc, manganese, silicone, iron, copper, nickel, beryllium, and the balance (remaining percentage) of magnesium result in truncated materials of negative potential producing magnesium alloy. Examples 1~3 in Table 1 show the ingredients in their wt %.

Comparative Examples

The composition of truncated materials in the comparative examples 1~3 are shown in the following Table 1.

TABLE 1

|  | Al | Zn | Mn | Si | Fe | Cu | Ni | Be | Mg |
| --- | --- | --- | --- | --- | --- | --- | --- | --- | --- |
| Example 1 | 8.89 | 0.6840 | 0.2169 | 0.0206 | 0.0020 | 0.0011 | 0.0007 | 0.0006 | Bal. |
| Example 2 | 8.80 | 0.6570 | 0.2235 | 0.0183 | 0.0020 | 0.0011 | 0.0007 | 0.0007 | Bal. |
| Example 3 | 8.80 | 0.6890 | 0.2319 | 0.0201 | 0.0020 | 0.0011 | 0.0008 | 0.0007 | Bal. |
| Comparative example 1 | 5.67 | 0.1740 | 0.1369 | 0.0206 | 0.0020 | 0.0011 | 0.0007 | 0.0006 | Bal. |
| Comparative example 2 | 6.87 | 0.3530 | 0.2368 | 0.0206 | 0.0020 | 0.0011 | 0.0007 | 0.0006 | Bal. |
| Comparative example 3 | 7.56 | 0.5640 | 0.3167 | 0.0206 | 0.0020 | 0.0011 | 0.0007 | 0.0006 | Bal. |

These contents in Examples 1~3 and Comparative examples 1~3 are used to make the product shown in FIG. 1. The length L and width W of the product are approximately 50 mm×50 mm; its thickness S is approximately 1 mm. This product is injected into the layer of bound calcium ions and magnesium ions forming the medium layer, and the upper layer composed of infrared substances, bamboo coal, anti-bacteria ceramics, energy ceramics and the tourmaline, and the bottom layer of alkaline ceramics; wherein 10–20 wt % of the magnesium alloy of the present invention binds with the medium layer, and wherein the aluminum, zinc and manganese have effects on the production of negative potential; their effects are shown as follows:

TABLE 2

|  | Negative potential status |
| --- | --- |
| Example 1 | ○ |
| Example 2 | ○ |
| Example 3 | ○ |
| Comparative example 1 | X |
| Comparative example 2 | X |
| Comparative example 3 | ● |

The sign "○" in Table 2 indicates excellent negative potential status, and the sign "x" indicates poor negative potential status. The table clearly indicates that the decrease in wt % of aluminum, zinc and manganese has effects on negative potential status. The sign "●" indicates excellent negative potential status. The table shows that the wt % readings of aluminum, zinc and manganese are close to the standard values.

After pure water is processed by the negative potential alkaline generator, the contents of the following ingredients are tested, including: (1) analysis of heavy metals: ICP, (2) chlorate: stability test, (3) nitrite nitrogen (nitrogen reading): NIEA W418.51C, (4) total tri-halogen methane: NIEA785.53B. Results of the above tests are shown in Table 3 (Report No. RI/2004/80007A-04). Apparently, no heavy metal is detected in the negative potential alkaline water. After pure water is taken and processed by the negative potential alkaline water generator, the following ingredients are found in the pure water, including: (1) total germ count: lab test conducted on a mixture of 50 cc of water after it is soaked for 15 minutes according to CNS 10890 and 150 cc of original water, (2) analysis of heavy metals: ICP, (3) pH value: pH meter. Results of the above test are shown in Table 4 (Report No. RI/2004/80007A-05). Obviously, the water quality after the immersion process is safe, containing 30.7 mg/L of calcium and 12.9 mg/L of magnesium. The pH value of tested water is 9.94, which is on the alkaline side.

TABLE 3

(Report No.: RI/2004/80007A-04)
TEST RESULT:

| TEST ITEM | | RESULT |
| --- | --- | --- |
| Cd | (mg/L) | Not detected |
| Pb | (mg/L) | Not detected |
| As | (mg/L) | Not detected |
| Hg | (mg/L) | Not detected |
| Cr | (mg/L) | Not detected |
| Ba | (mg/L) | Not detected |
| Se | (mg/L) | Not detected |
| Cyanogen (CN—) | (—) | Not detected |

TABLE 3-continued (Report No.: RI/2004/80007A-04)
TEST RESULT:

| TEST ITEM | | RESULT |
| --- | --- | --- |
| Nitrite-Nitrogen (as N) | (—) | Not detected |
| THMs | (mg/L) | 0.00497 |

---oOo---

TABLE 4

(Report No.: RI/2004/80007A-05)
TEST RESULT:

| TEST ITEMS | | RESULT |
| --- | --- | --- |
| Total Plate Count | | |
| In Tap Water | (CFU/ml) | $3.4 \times 10^1$ |
| In Filtrate + Tap Water | (CFU/ml) | Not detected |
| pH Value | (—) | 9.94 |
| Na | (mg/L) | 28.6 |
| K | (mg/L) | 8.52 |
| Ca | (mg/L) | 30.7 |
| Mg | (mg/L) | 12.9 |

---oOo---

Furthermore, the finished product of the present invention of magnesium alloy can be made in a powder form and coated on the surface of infrared substances, anti-bacteria ceramics and alkaline ceramics, as a demonstration of another effect of the present invention.

What is claimed is:

1. An article comprising a material layer, said material layer being formed by binding a magnesium alloy with calcium ions and magnesium ions; said magnesium alloy producing negative potential comprising: 8–9.1 wt % Al, 0.1–1.0 wt % Zn, 0.1–1.0 wt % Mn, 0.05 wt % or less Si, 0.002 wt % or less Fe, 0.00 12 wt % or less Cu, 0.0009 wt % or less Ni, 0.0008 on less wt % of Be, and a remaining percentage of magnesium.

2. The article as in claim 1, wherein the magnesium alloy is in a powder form.

3. The article as in claim 1, wherein the material layer is bound with an upper layer comprising infrared substances, bamboo coal, anti-bacteria ceramics, energy ceramics or tourmaline and a bottom layer of alkaline ceramic particles.

4. The article as in claim 3, wherein 10–20 wt % of the magnesium alloy binds with the material layer.

5. An article comprising a material layer, said material layer being formed by binding a magnesium alloy with calcium ions and magnesium ions; said magnesium alloy producing negative potential comprising: 5–9.1 wt % Al, 0.1–1.0 wt % Zn, 0.1–1.0 wt % Mn, 0.01–0.03 wt % Si, 0.002 wt % or less Fe, 0.0010–0.0012 wt % Cu, 0.0009 wt % or less Ni, 0.0008 wt % or less Be, and a remaining percentage of magnesium.

6. The article as in claim 5, wherein the material layer is coupled with an upper layer comprising infrared substances, bamboo coal, anti-bacteria ceramics, energy ceramics, or tourmaline and a bottom layer of alkaline ceramic particles.

7. The article as in claim 5, wherein 10–20 wt % of the magnesium alloy binds with the material layer.

8. The article as in claim 5, wherein the magnesium alloy is in a powder form.

* * * * *